United States Patent [19]

Connelly

[11] 4,048,240
[45] Sept. 13, 1977

[54] METHOD OF OXIDIZING OR BLEACHING A CONTAMINANT IN A NON-AQUEOUS FLUID

[76] Inventor: Robert Frederick Connelly, Akasaka P.O. Box 10, Tokyo 107-91, Japan

[21] Appl. No.: 733,877

[22] Filed: Oct. 19, 1976

[30] Foreign Application Priority Data

Oct. 22, 1975  Japan .................... 50-126445

[51] Int. Cl.$^2$ .................... C07C 9/00; C07C 19/00
[52] U.S. Cl. .................... 260/652 P; 260/676 AD; 8/108 R; 8/142; 8/DIG. 20; 208/289
[58] Field of Search .................... 208/289, 299, 301, 236, 208/241, 254 R; 260/652 P, 654 S, 674 SA, 676 AD; 8/108 R

[56] References Cited

U.S. PATENT DOCUMENTS

| | | | |
|---|---|---|---|
| 1,812,426 | 6/1931 | Apgar | 208/299 |
| 1,940,592 | 12/1933 | Henderson | 8/108 R |
| 2,309,871 | 2/1943 | Schulze et al. | 260/676 AD |
| 2,849,120 | 8/1958 | McMichael et al. | 208/299 |
| 2,882,120 | 4/1959 | Stoddard, Jr. | 8/108 R |

*Primary Examiner*—George Crasanakis

[57]. ABSTRACT

Nitrogen trichloride produced in situ from the reaction of a chlorine source and a nitrogen source in a non-aqueous fluid is adsorbed on an adsorption media and serves to oxidize, bleach or deactivate contaminants and foreign matter of the fluid similarly adsorbed on said adsorption media.

6 Claims, No Drawings

METHOD OF OXIDIZING OR BLEACHING A CONTAMINANT IN A NON-AQUEOUS FLUID

BACKGROUND OF THE INVENTION

In the past, hypochlorite ions or chlorine have been employed as oxidants and deodorants, bleaching agents and bacteriastats. However, these agents are useless in hydrocarbon and halogenated hydrocarbon fluids in which they are insoluble.

Further, various forms of activated carbon have been used to remove small quantities of liquid or gaseous substances from fluid media (liquids or gases). However, the available adsorption sites are eventually saturated resulting in depletion of the media.

While nitrogen trichloride has long been known as a strong oxidizing agent, its use has been restricted by its toxic and explosive characteristics. This volatile lipophilic liquid is almost insoluble in aqueous solutions and therefore sinks to the bottom of aqueous solutions to form concentrated pools of extremely corrosive and explosive liquid; gaseous nitrogen trichloride, on the other hand, rises to mix with the air above its solution forming an explosive and toxic mixture. However, in hydrocarbon or halogenated hydrocarbon fluids, nitrogen trichloride is quite soluble and rapidly becomes dispersed throughout the fluid where it is dangerous only when in concentration of over 12% and is exposed to a source of ignition. It can be used as an oxidizing agent for solids or liquids suspended in hydrocarbon or halogenated hydrocarbon fluids if the following conditions are met:

A. The addition method is such that the $NCl_3$ concentration never exceeds 10% but is always high enough (often less than 2 mg/l to meet the oxidizing requirements of the contaminant being oxidized, bleached or deactivated.

B. The nitrogen trichloride can be intimately united with the contaminant being bleached by adsorbing it and the contaminant on an adsorption medium.

DESCRIPTION OF INVENTION

This invention provides a method for introducing active chlorine in the form of nitrogen trichloride to a contaminated stream of hydrocarbon or halogenated hydrocarbon fluids or other fluids or mixture of same controlled in such a way that critical solubility problems do not occur and deleterious effects do not affect personnel or equipment. After introducing the active chlorine compound in the fluid medium, it is passed through a column of activated carbon, where both the chlorine compound and the foreign ingredients are adsorbed. Under these conditions a unique situation occurs in which high concentrations of active chlorine and foreign contaminants meet on the adsorption medium, resulting in rapid and complete reaction and the total destruction or deactivation of the contaminants. The fluid stream leaving the adsorption column is also purified, deodorized and decolorized. The combination of the controlled amounts of nitrogen trichloride and the active carbon thereby provide a synergistic effect which is far in excess of that which would result from the use of either medium alone.

More specifically, a few parts per million of a nitrogen compound (amine, urea or similar compound) is dissolved or dispersed in a non-aqueous fluid where it may either be considered as an additive or a contaminant. This fluid is then passed over a chlorine source such as trichloroisocyanuric acid or alkaline earth hypochlorite. The nitrogen compound in the fluid is then able to react with the chlorine to produce oil soluble nitrogen trichloride.

$$CO(NH_2)_2 + 2HOCl \rightarrow 2 NH_2Cl + CO_2 + H_2O$$
$$NH_2Cl + 2HOCl \rightarrow NCl_3 + 2H_2O$$

The reaction rate is directly proportional to the rate of flow of the fluid and the concentration of nitrogen compound dispersed or dissolved therein. Immediately down stream of the above, an activated carbon, Fuller's earth activated bauxite column adsorbs the contaminants and the nitrogen trichloride from the fluid. The two chemicals react to produce volatile, odorless, colorless or otherwise innocuous end products.

A commerical use for this invention was found in a laundry which uses perchlorethylene to degrease and clean mechanic's uniforms. Bleaching must be done by an expensive, separate water operation. The separate water bleach was eliminated by using buffered isocyanuric acid tablets in the last solvent rinse flow stream entering the wheel. The natural animal amines left in the solvent from the previous wash reacted with the hypochlorite from the chlorine source to produce a few parts per million of nitrogen trichloride some of which bleached and disinfected the uniforms. On leaving the wheel, the solvent was passed through a carbon column where the remaining nitrogen trichloride was utilized in purifying the fluid. When sufficient natural amines were not present in the fluid in the winter months, 10 parts per million of a 5% ammonia solution was dispersed into the solvent flow upstream of the isocyanuric acid tablets. By adjusting the solution injection and flow rate, an excellent bleach and sterilization was achieved.

This process is particularly suitable for use in waste disposal systems employing non-aqueous fluids (hydrocarbons, halocarbons or similar media or mixtures thereof) to transport the waste. The color bodies, nitrogen compounds, mercaptans, methyl indole, musk and similar odor and color substances extracted by the fluid from these wastes are effectively neutralized by this process. The active chlorine may be added in a number of forms such as trichloroisocyanuric acid, hypochlorite or similar substances. Urea contained in small amounts of urine (from 15–200,000 mg/l of organic fluid) in the organic fluid combine with the active chlorine, resulting in the production of nitrogen trichloride. The nitrogen trichloride and contaminants are then adsorbed on activated carbon, Fuller's earth or activated bauxite to increase the reaction concentrations as described above. These combined mechanisms result in the production of a fluid medium from which color, bacteria, odor, moisture, acids and other deleterious ingredients have been removed; further, there are almost no chlorine or hypochlorous compounds present in the effluent non-aqueous fluid medium.

Another function for this process is in the bleaching of materials that are not successfully, safely or conveniently immersed in aqueous solutions. For example, parts, thread or fabric composed of silk, wool, nylon or other nitrogen based polymers may be immersed and cleaned in a non-aqueous fluid medium containing dispersions of a few parts per million of water solutions of amines such as ammonia or urea. Some of the fluid is pumped in a side loop over a solid chlorine source (hypochlorite, chlorinated isocyanuric acid, or similar compound) where the amine reacts to produce nitrogen trichloride in situ intimately dispersed in the fluid. When the activated fluid returns to the bleach bath, the dispersed nitrogen trichloride rapidly becomes adsorbed on the surface of the composition to be bleached, where it reacts with oxidizable contaminants, dyes, bacteria, viruses or soil, thereby, substances otherwise sensitive to water solutions of chlorine may be treated without adverse effects.

The most convenient chlorine source has been found to be trichloroisocyanuric acid which is extensively used as an industrial laundry bleach and as a swimming pool disinfectant. It is available in blocks, tablets and granular forms. The tablet form usually is found to have the right combination of structural permanence and available surface area to allow it to sit in a hydrocarbon process stream giving out chlorine only when supplied moisture and amine.

In moisture, trichloroisocyanuric acid is slightly soluble (1.5-2 gr/100 gr $H_2O$) and gives off hypochlorous acid, mono and di-chloroisocyanuric acid and isocyanuric acid.

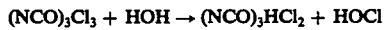

$(NCO)_3Cl_3 + HOH \rightarrow (NCO)_3HCl_2 + HOCl$

$(NCO)_3HCl_2 + HOH \rightarrow (NCO)_3H_2Cl + HOCl$

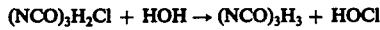

$(NCO)_3H_2Cl + HOH \rightarrow (NCO)_3H_3 + HOCl$

But in an unbuffered solution, the hypochlorite can attack the remaining chloroisocyanuric acid to bring about ring de-composition which prematurely gives off $NCl_3$.

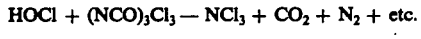

$HOCl + (NCO)_3Cl_3 \rightarrow NCl_3 + CO_2 + N_2 +$ etc.

This reaction is to be avoided if the $NCl_3$ is to be strictly limited to that produced by the amine activator. The rate of decomposition is increased by low pH or high temperatures and with high concentrations of hypochlorous chlorine in the available moisture. Premature decomposition can therefore be kept to a minimum by maintaining a low temperature, limiting the moisture content (and therefore the hypochlorite) to just that which is combined with the amine and by alkaline buffering the tablets to a pH of 7-8. Alkaline buffers such as carbonates and sodium-meta silicate have been used with success. The appropriate buffer is selected on the basis of flow rate, amine availability and activity desired since an increased pH (above 9) also greatly increases trichloroisocyanuric acid solubility and hypochlorate formation.

Precautions specific to hypochlorites and hypochlorite sources should be observed in use of this invention. The chlorine source should be handled in due respect to its ability to produce corrosive and irritating products and to cause explosions or fires if carelessly handled. The carrier fluid should be one that is not easily attacked by chlorine or chlorine sources. Specifically, highly unsaturated hydrocarbons such as turpentine should not be used; nor should the alcohols.

Beneficial Effects of the Invention

A. Use of an active chlorine compound to oxidize or bleach contaminants suspended in a non-aqueous fluid medium.

B. A method for safely utilizing nitrogen trichloride to bleach and oxidize contaminants.

C. A method for bleaching materials, parts and fabrics (cottons, plastics, nylon, silk or polyamids) suspended in a non-aqueous fluid medium such as a dry cleaning fluid.

D. A means for making the rate of addition of chloroamine bleach such as $NCl_3$ to a fluid stream with variable flow rates automatically dependent on that flow rate thereby overcoming the usual problems of toxicity, corrosion and fluid deterioration that would result from merely adding excesses of the chloroamine to assure adequate dosage.

That which is sought to be protected is set forth in the following claims.

What is claimed is:

1. A method for oxidizing or bleaching a contaminant in a non-aqueous fluid which comprises forming nitrogen trichloride in situ by the reaction of a chlorine source and a nitrogen source in said fluid, and adsorbing said contaminant and said nitrogen trichloride on a solid adsorbent, and recovering said fluid substantially free of acid contaminant.

2. The method of claim 1 wherein said chlorine source is selected from the group consisting of trichloroisocyanuric acid and alkaline earth hypochlorites.

3. The method of claim 1 wherein said nitrogen source is selected from the group consisting of amines and urea.

4. The method of claim 1 wherein said nitrogen trichloride concentration in the fluid is less than 10% but sufficient for oxidizing said contaminant.

5. The method of claim 1 wherein said adsorbent is selected from the group consisting of carbon, Fuller's earth and activated bauxite.

6. The process of claim 1 wherein said non-aqueous fluid is selected from the group consisting of hydrocarbons and halogenated hydrocarbons.

* * * * *